United States Patent [19]

Gitlitz

[11] 4,058,545
[45] Nov. 15, 1977

[54] METHOD FOR PREPARING TRI(β-SUBSTITUTED PHENETHYL)TIN HALIDES

[75] Inventor: Melvin H. Gitlitz, Edison, N.J.

[73] Assignee: M&T Chemicals Inc., Greenwich, Conn.

[21] Appl. No.: 711,202

[22] Filed: Aug. 3, 1976

[51] Int. Cl.$^2$ .............................................. C07F 7/22
[52] U.S. Cl. ................................................. 260/429.7
[58] Field of Search ..................................... 260/429.7

[56] References Cited

U.S. PATENT DOCUMENTS

| | | | |
|---|---|---|---|
| 3,010,979 | 11/1961 | Ramsden | 260/429.7 |
| 3,607,891 | 9/1971 | Kushlefsky et al. | 260/429.7 |
| 3,657,451 | 4/1972 | Horne | 260/429.7 X |
| 3,789,057 | 1/1974 | Reifenberg et al. | 260/429.7 |
| 3,849,460 | 11/1974 | Daniels et al. | 260/429.7 |

OTHER PUBLICATIONS

Reichle, Inorg. Chem., V5, pp. 87–91 (1966).
Limmer et al., J. Org. Chem., V31, pp. 3857–3860 (1966).

*Primary Examiner*—Helen M. S. Sneed
*Attorney, Agent, or Firm*—Robert P. Auber; Kenneth G. Wheeless; Robert Spector

[57] ABSTRACT

Tri(β-substituted phenethyl)tin halides such as trineophyltin chloride are prepared by reacting three moles of the corresponding organomagnesium halide for every mole of an organotin trihalide containing an alkyl or a phenyl group bonded to the tin atom. The resultant tetraorganotin compound is reacted with an anhydrous stannic halide in a hydrocarbon diluent and the desired triorganotin halide is isolated following hydrolysis of the reaction mixture.

5 Claims, No Drawings

METHOD FOR PREPARING TRI(β-SUBSTITUTED PHENETHYL)TIN HALIDES

BACKGROUND

This invention relates to a method for preparing triorganotin compounds. This invention further relates to a method for preparing a specific class of triorganotin halides in high yield and purity using a method which heretofore has been of limited use, since it was considered operable only for a relatively small group of triorganotin halides.

A general method for preparing triorganotin halides wherein the hydrocarbon groups bonded to the tin atom are (1) cycloalkyl, (2), a combination of cycloalkyl and alkyl or (3) combinations of two groups differing in molecular weight by at least 42 are disclosed in U.S. Pat. Nos. 3,607,891 and 3,789,057. In accordance with this method, a tetraorganotin compound containing two different hydrocarbon groups is reacted with an equimolar amount of a stannic halide. Up until now attempts to apply this method to tetraorganotin compounds other than the types disclosed in the two aforementioned patents have yielded virtually inseparable mixtures of at least two triorganotin halides resulting from nonselective cleavage of the hydrocarbon groups bonded to the tin atom. It has now been found that when the aforementioned tetraorganotin compounds contain three β-substituted phenethyl groups of the general formula

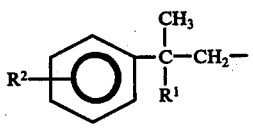

and one linear hydrocarbon or phenyl group, the one dissimilar hydrocarbon group is readily cleaved and replaced by a halogen atom when the tetraorganotin compound is reacted with a stannic halide. $R^1$ in the foregoing formula can be hydrogen or a linear hydrocarbon radical. Surprisingly, the present method is not useful when the methyl group of the foregoing formula and $R^1$ are both hydrogen.

SUMMARY OF THE INVENTION

This invention provides a method for preparing triorganotin compounds of the general formula

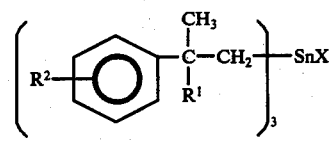

wherein $R^1$ represents hydrogen or methyl, $R^2$ is selected from the group consisting of hydrogen, alkyl containing from 1 to 6 carbon atoms and X is chlorine or bromine, said method consisting essentially of the following steps:

1. Reacting at least three moles of an organomagnesium halide,

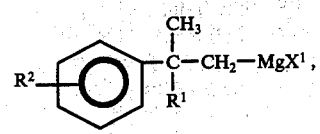

where $R^1$ and $R^2$ are as defined above for each mole of an alkyltin trihalide, $R^3 SnX_2^2$ wherein $X^1$ and $X^2$ are individually selected from the group consisting of chlorine and bromine and $R^3$ is phenyl or a linear hydrocarbon group containing from 1 to 8 carbon atoms;

2. Reacting the resultant tetraorganotin compound with an equimolar amount of an anhydrous stannic halide, $SnX_4$, in a liquid hydrocarbon diluent and isolating said triorganotin compound by combining the reaction mixture with water or a dilute aqueous acid solution.

DETAILED DESCRIPTION OF THE INVENTION

The present class of triorganotin halides wherein the halogen is chlorine or bromine is prepared by reacting at least three moles of the corresponding organomagnesium halide,

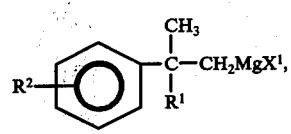

for every mole of an alkyl- or phenyltin trihalide, $R^3 SnX_3^2$, wherein $R^3$ is phenyl or a linear hydrocarbon. When $R^3$ is alkyl it contains from 1 to 8 carbon atoms. Alternatively $R^3$ may contain a double bond between two adjacent carbon atoms. In the foregoing formulae, X, $X^1$ and $X^2$ are individually selected from chlorine and bromine. Preferably $R^1$ is methyl.

The reaction between the organomagnesium halide and the organotin trihalide yields a tetraorganotin compound of the general formula

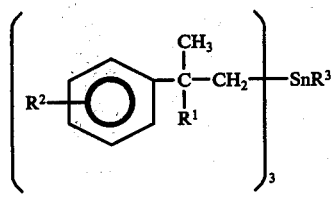

which is subsequently reacted with an equimolar amount of a stannic halide, $SnX_4$. During this reaction the hydrocarbon group represented by $R^3$ is replaced by a halogen atom from the stannic halide.

The organotin trihalide, $R^3SnX_3^2$, can be prepared by reacting the corresponding alkyl halide, $R^3X^2$, with a stannous halide, $SnX_2$, as described in U.S. Pat. No. 3,340,283, the pertinent sections of which are hereby incorporated by reference.

The reaction between the stannic halide and tetraorganotin compound is performed under anhydrous conditions at temperatures from about −25° to 80° C, preferably from +25 to 80° C. in a hydrocarbon solvent. Preferred solvents include pentane, hexane and cyclohexane.

Preferably the stannic halide is dissolved in the organic hydrocarbon and the resultant solution is added dropwise to a second solution containing the tetraorganotin compound in the same solvent. The temperature of the reaction mixture is preferably maintained below about 30° C. during the addition, which requires about one hour, after which the mixture is heated to a temperature from 35° to 80° C. Preferably the temperature employed is the reflux temperature of the reaction mixture. Heating is continued for from about 15 to 60 minutes to ensure complete reaction. The reaction mixture is then allowed to cool to ambient temperature, whereupon it is combined with one or more portions of water or a dilute aqueous acid solution. The by-product of the reaction, a monoorganotin trihalide, $R^3SnX_3$, is soluble in the aqueous phase. The desired product remains in the organic solvent, and is readily isolated by evaporating the solvent. No further purification is usually required, however the product can be recrystallized if desired. The organic solvent is preferably freed of any water remaining following the extraction step. Any of the conventional chemical dehydrating agents are suitable, provided that they will not react with either the triorganotin halide or the solvent. Preferred drying agents include anhydrous magnesium sulfate, anhydrous sodium sulfate and anhydrous calcium sulfate.

The by-product monoorganotin trihalide can be recycled by reacting it with the aforementioned organomagnesium compound.

The present triorganotin halides are solids at ambient temperature. The halides can readily be converted to other derivatives such as the oxide, acetate and sulfate using known reactions. The desired anionic radical can be introduced by reacting the corresponding triorganotin halide, hydroxide or bis(triorganotin) oxide with the reagent indicated in the following table.

| ORGANOTIN DERIVATIVE | + REAGENT → | DESIRED PRODUCT |
|---|---|---|
| Chloride or Bromide | Carboxylic acid + acid acceptor, e.g. pyridine | carboxylate, e.g. acetate |
| " | alkali metal salt of a carboxylic acid | " |
| " | aqueous solution of alkali metal hydroxide | oxide (or hydroxide) |
| " | alkali metal alkoxide or alcohol + acid acceptor (e.g. an amine) | alkoxide |
| " | alkali metal phenoxide or phenol + acid acceptor | phenoxide |
| " | potassium fluoride or hydrofluoric acid | fluoride |
| " | alkali metal sulfide | sulfide |
| " | alkali metal sulfate | sulfate |
| " | mercaptan + acid acceptor | mercaptide |
| Oxide or Hydroxide | carboxylic acid or anhydride | carboxylate |
| " | alcohol (or phenol) | alkoxide (or phenoxide) |
| " | hydrofluoric acid | fluoride |
| " | dilute (10-25 weight %) aqueous sulfuric acid | sulfate |
| " | hydrogen sulfide | sulfide |
| " | alkyl or aryl mercaptan | mercaptide |

The reaction conditions such as preferred solvents, temperatures and reaction times for preparing the derivatives summarized in the preceding table are known in the art and, therefore, do not require a detailed description in the present specification. A comprehensive treatment of this subject matter together with numerous literature references is contained in an article by R. D. Ingham et al. that appeared in the October, 1960 issue of CHEMICAL REVIEWS (pp. 459-539). The aforementioned derivatives may be liquids or solids at ambient temperature, depending upon the type of substituents represented by X or Y.

Triorganotin compounds prepared in accordance with the present method effectively control mites when applied to living plants that are susceptible to infestation by these insects. This fact is disclosed in U.S. Pat. No. 3,657,451. A single application of these compounds to living plants or other substrates can provide residual and extended control of mites for a considerable period of time, the duration of which is dependent to some extent upon mechanical and biological influences, including weather. Formulations containing the present organotin compounds can be applied directly onto mites.

In preparing compositions for application to plants the organotin compound is often augmented or modified by combining it with one or more commonly employed pesticide additives or adjuvants including organic solvents, water or other liquid carriers, surfactants to aid in dispersing or emulsifying the organotin compound or particulate and finely comminuted or divided solid carriers. Depending upon the concentration of triorganotin compound in these compositions, or as liquid concentrates which are subsequently diluted with one or more additional inert liquids to produce the ultimate treating compositions. In compositions employed as concentrates, the triorganotin compound can be present at concentrations of from about 5 to about 98% by weight. Other biologically active agents that are chemically compatible with the present triorganotin compounds can also be included in the concentrate.

The optimally effective concentration of tin compounds to be employed as toxicant in a composition is dependent upon whether the mite is contacted with or ingests the toxicant. The actual weight of compound constituting an effective dose is primarily dependent upon the susceptibility of the mite to the particular triorganotin compound. For control of spider mites, good results are obtained with liquid or dust compositions containing as little as 25 parts per million by weight of toxicant. Compositions containing up to 90 percent by weight of toxicant can be employed to treat a heavily infested area.

In the preparation of dust compositions, the organotin compound can be blended with many commonly employed finely divided solid carriers such as fuller's earth, attapulgite, bentonite, pyrophyllite, vermiculite, diatomaceous earth, talc, chalk, gypsum and wood flour. The carrier, usually in a finely divided form, is ground or mixed with the toxicant or wetted with a dispersion of the toxicant in a volatile liquid. Depending upon the relative proportions of toxicant and carrier, these compositions can be employed as concentrates that are subsequently diluted with additional solid carrier to obtain the desired amount of active ingredient. Alternatively, such concentrate dust compositions can be employed in combination with various known anionic, cationic or non-ionic surfactants as emulsifying or dispersing agents to form spray concentrates. Such concentrates are readily dispersible in liquid carriers to form spray compositions or other liquid formulations containing the toxicants in any desired amount. The choice and concentration of surfactant are determined by the ability of the material to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene and petroleum distillates. Among the preferred petroleum distillates are those boiling under 400° F. at atmospheric pressure and having a flash point above about 80° F.

Liquid compositions can also be prepared by dissolving one of the present triorganotin compounds in a mixture containing a water-immiscible organic liquid and a surfactant agent. The resultant emulsifiable concentrate is then further diluted with water and an oil to form spray mixtures in the form of oil-in-water emulsions. In such compositions, the carrier comprises an aqeuous emulsion, i.e. a mixture of water-immiscible solvent, emulsifying agent and water. Preferred surfactants for these compositions are oil soluble and include the condensation products of alkylene oxides with phenols and organic and inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthetic organic oils. The concentration of surfactant in the liquid dispersions and aqueous emulsions is from about 1 to about 20 percent by weight of the combined weight of surfactant and triorganotin compound.

When operating in accordance with the present invention, the organotin compound or a composition containing the compound can be applied directly onto the mite or to the site to be protected, particularly plants and trees. Application to the foilage of plants is conveniently carried out using power dusters, boom sprayers and spray dusters. When employed in this manner the compositions should not contain any significant amounts of phytotoxic diluents. In large scale operations, dusts or low volume sprays may be applied from an aircraft.

The following Example 1 represents a preferred embodiment of the present method and is not intended to limit the scope of the accompanying claims. All parts and percentages are by weight unless otherwise specified.

EXAMPLE 1

Preparation of Trineophyltin Chloride

A. Preparation of Butyltrineophyltin

To 24.3 g. (1 g. atom) of magnesium turnings heated to a temperature of 40° C. under a nitrogen atmosphere was added a 25 cc. portion of a solution containing 168.6 g. (1 mole) of neophyl chloride dissolved in 270 cc. of anhydrous tetrahydrofuran. The reaction was initiated using a few drops of ethylene dibromide. The remaining portion of the neophyl chloride solution was gradually added during a period of 1 hour while the reaction mixture was heated to the boiling point. Heating was continued for an additional 2 hours following completion of the addition. The reaction mixture was allowed to cool to ambient temperature and remain at this temperature for about 16 hours, during which time stirring of the mixture was continued. At the end of this period all of the magnesium appeared to have reacted.

A 315 g. portion of the resultant solution, containing 0.725 mole of neophylmagnesium chloride was added dropwise to a stirred solution of butyltin trichloride (56.4 g., 0.2 mole) dissolved in 250 cc. of dry toluene. The addition required 1.5 hours and was conducted under a nitrogen atmosphere. During the addition the temperature of the reaction mixture was maintained below 45° C. Following completion of the addition the reaction mixture was heated to the boiling point (92° C.) for one hour, then allowed to cool to ambient temperature. To the resultant mixture was added a solution containing 250 cc. water and 25 g. citric acid. The aqueous phase of the resultant mixture was then separated and discarded. The water present in the organic phase of the resultant two phase liquid was removed by combining the organic phase with a portion of anhydrous magnesium sulfate, which was subsequently removed by filtration. The solvent was evaporated under reduced pressure to yield 133.7 g. of a yellow oily liquid. The product was distilled under reduced pressure (105° C. and 0.12 mm. Hg.) to remove additional by-products. The residue, a liquid weighing 111.7 g., was isolated and exhibited a refractive index ($n_D^{26}$) of 1.5630. Analysis by vapor phase chromatography indicated that the product was 94.5% pure.

B. Cleavage of Butyltrineophyltin to Trineophyltin Chloride

A 43.1 g. (0.075 mole) portion of the butyltrineophyltin prepared as described in part A of this example was dissolved in 150 cc. of hexane. To this solution was added a solution containing 19.5 g. (0.075 mole) of stannic chloride and 100 cc. hexane. The addition required 20 minutes, following which the resultant mixture was heated to the boiling point (70° C.) for 20 minutes and then allowed to cool to ambient temperature. A 100 cc. portion of the solution obtained by combining 8 cc. of 12N aqueous hydrochloric acid and 194 cc. water was then added to the reaction mixture, whereupon a white solid precipitated. An additional 100 cc. of the aqueous hydrochloric acid was then added, and the mixture was stirred for five minutes. The solid phase was then isolated by filtration and dried to yeild 30.0 g. of a white solid melting from 113°–116° C. The product was found to contain 21.85% tin and 6.77% chlorine. The calculated values for trineophyltin chloride are 21.44% tin and 6.40% chlorine. Vapor phase chromatography indicated that the compound was 99.55% pure.

Trineophyltin chloride was also prepared by reacting 29.8 g. (0.05 mole) of phenyltrineophyltin with 13.0 g. (0.05 mole) of anhydrous stannic chloride dissolved in a mixture containing 75 cc. benzene and 125 cc. hexane. The resultant mixture was heated at the boiling point (71° C.) for five minutes then reacted with a dilute hydrochloric acid solution to yield tri(neophyl)tin chloride. The product exhibited a melting range of 117°–119° C. following one recrystallization from 150 cc. of isopropanol.

Phenyltrineophyltin and methyltrineophyltin were prepared using a procedure similare to that disclosed hereinabove for butyltrineophyltin.

EXAMPLE 2

Attempted Preparation of Tri($\beta$-phenethyl)tin Chloride

This example demonstrates that the present method is unsuitable for preparing a compound which is structurally analogous to trineophyltin chloride.

A. Preparation of Butyl Tri(β-phenethyl)tin

To 12.16 g. (0.5 g. atom) of magnesium turnings heated to a temperature of 40° C. under a nitrogen atmosphere was added a 20 cc. portion of a solution containing 92.5 g. (0.5 mole) of 2-bromoethylbenzene dissolved in 450 cc. of anhydrous tetrahydrofuran. When the reaction initiated the remaining portion of the 2-bromoethylbenzene solution was gradually added during a period of one hour while the reaction mixture was heated to the boiling point. Heating was continued for an additional 45 minutes, then the reaction mixture was allowed to cool to ambient temperature, at which time a small amount (0.60 g.) of unreacted magnesium was removed. Upon analysis the product was found to contain 0.78 mole of β-phenethylmagnesium bromide per kilogram of solution.

A solution containing 22.6 g. (0.08 mole) of butyltin trichloride and 250 cc. of anhydrous benzene was added gradually over a period of 1 hour to a portion of the aforementioned β-phenethylmagnesium bromide solution containing 0.24 mole of the organomagnesium compound. The reactor contained a nitrogen atmosphere. During the addition the temperature of the reaction mixture was maintained below 45° C. Following completion of the addition the contents of the reactor were heated to the boiling point for one hour, then allowed to cool to ambient temperature. To the resultant mixture was added a solution containing 300 cc. water and 25 g. citric acid. The aqueous phase of the resultant mixture was removed and discarded. The water present in the organic phase was removed using a portion of anhydrous magnesium sulfate, which was subsequently separated by filtration and discarded. The solvent was then evaporated under reduced pressure to yield 39.52 g. of a yellow liquid exhibiting a refractive index $(N_D{}^{23})$ 1.5722. The product was found to contain 22.94% tin and 0.09% chlorine. The calculated values for butyl tri(β-phenethyl)tin are 24.16% tin and 0.0% chlorine.

B. Cleavage of Butyl Tri(β-phenethyl)tin to Tri(β-phenethyl)tin Chloride

A 17.2 g. (0.035 mole) portion of the butyl tri(β-phenethyl)tin prepared as described in part A of this example was dissolved in 50 cc. of pentane. To this solution was added a solution containing 9.1 g. (0.035 mole) of stannic chloride and 50 cc. pentane. The addition required 20 minutes, following which the resultant mixture was heated to the boiling point (40° C.) for 30 minutes and then allowed to cool to ambient temperature. One half of a solution obtained by combining 4 cc. of 12N aqueous hydrochloric acid and 200 cc. water was then added to the reaction mixture with vigorous stirring both during the addition and for three minutes thereafter. The organic layer of the resultant two-phase liquid was isolated and combined with the remainder of the aforementioned aqueous hydrochloric acid solution. The organic layer was again isolated and the water therein removed using a quantity of anhydrous magnesium sulfate. The pentane was then evaporated under reduced pressure to yield 15.14 g. of a yellow liquid exhibiting a refractive index $(n_D{}^{24})$ of 1.5837.

Analysis of the product by vapor phase chromatography revealed two major components present in equivalent amounts (48.5 and 45.3% by volume). Unreacted starting material comprised 0.8% of the total. This demonstrates that the present method cannot be employed to prepare tri(β-phenethyl)tin chloride in high yield and purity.

What is claimed is:

1. A method for preparing a triorganotin halide of the general formula

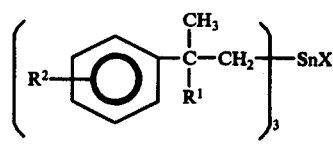

wherein $R^1$ represents hydrogen or methyl, $R^2$ is selected from the group consisting of hydrogen, alkyl contaning from 1 to 6 carbon atoms and X is chlorine or bromine, said method consisting essentially of the following steps:

1. Reacting at least three moles of an organomagnesium halide,

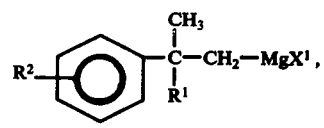

with each mole of an alkyltin trihalide, $R^3SnX_3{}^2$ wherein $X^1$ and $X^2$ are individually selected from the group consisting of chlorine and bromine and $R^3$ is phenyl or a linear hydrocarbon group containing from 1 to 8 carbon atoms;

2. Reacting the resultant tetraorganotin compound with an equimolar amount of an anhydrous stannic halide, $SnX_4$, in a liquid hydrocarbon diluent and isolating said triorganotin compound by combining the reaction mixture with water or a dilute aqueous acid solution.

2. A method according to claim 1 wherein $R^1$ is methyl, $R^2$ is hydrogen and $R^3$ is selected from the group consisting of alkyl, alkenyl and phenyl.

3. A method according to claim 2 wherein $R^3$ is methyl, butyl or phenyl.

4. A method according to claim 1 wherein X, $X^1$ and $X^2$ are chlorine.

5. A method according to claim 1 wherein said liquid hydrocarbon diluent is hexane, heptane, benzene or toluene.

* * * * *